(12) United States Patent
Walker et al.

(10) Patent No.: US 9,847,009 B2
(45) Date of Patent: Dec. 19, 2017

(54) CONNECTION CONFIRMATION USING ACOUSTIC DATA

(71) Applicant: Toyota Motor Engineering & Manufacturing North America, Inc., Erlanger, KY (US)

(72) Inventors: Jake Ryan Walker, Cambridge (CA); Touraj Pejouyan, Oakville (CA); Slavko Saric, Kitchener (CA); Jason James Dennis, Breslau (CA); Gregory Joseph Healy, Kitchener (CA); John D. Purse, Belwood (CA); Amit Bhalla, Brampton (CA)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 174 days.

(21) Appl. No.: 14/866,919

(22) Filed: Sep. 26, 2015

(65) Prior Publication Data

US 2017/0092099 A1 Mar. 30, 2017

(51) Int. Cl.
*G08B 21/18* (2006.01)
(52) U.S. Cl.
CPC .................................. *G08B 21/18* (2013.01)
(58) Field of Classification Search
CPC H01R 13/641; H01R 12/716; H01R 13/6272; H01R 13/639; H01R 13/64; G08B 21/18
See application file for complete search history.

(56) References Cited

U.S. PATENT DOCUMENTS

| | | | |
|---|---|---|---|
| 5,308,261 A | 5/1994 | Kightlinger | |
| 6,351,210 B1 * | 2/2002 | Stewart | B60R 22/48 180/268 |
| 6,457,991 B1 | 10/2002 | Yu | |
| 6,471,539 B1 | 10/2002 | Yu | |
| 7,199,703 B2 * | 4/2007 | Okita | B60R 22/48 280/801.1 |
| 7,639,125 B2 * | 12/2009 | Federspiel | B60N 2/002 180/271 |
| 2004/0155765 A1 * | 8/2004 | Okita | B60R 22/48 340/457.1 |
| 2007/0205884 A1 * | 9/2007 | Federspiel | B60N 2/002 340/457.1 |
| 2008/0008044 A1 * | 1/2008 | Patterson | G01S 5/22 367/128 |
| 2014/0203945 A1 | 7/2014 | Benner et al. | |

* cited by examiner

*Primary Examiner* — Sisay Yacob
(74) *Attorney, Agent, or Firm* — Christopher G. Darrow; Darrow Mustafa PC

(57) ABSTRACT

Arrangements related to the confirmation of component connections made during manufacturing or assembly processes are described. Acoustic data resulting from the connection can be received by a microphone. A controller can analyze the acoustic information to determine if a predetermined acoustic signature is present in the acoustic information. Responsive to the determination, a confirmation signal can be generated and transmitted by the controller. One or both of the microphone and controller can be included in a wearable device and worn by a user. In some arrangements, a motion sensor can be included in the wearable device to allow determination whether motion data during a connection is acceptable.

18 Claims, 6 Drawing Sheets

US 9,847,009 B2

CONNECTION CONFIRMATION USING ACOUSTIC DATA

FIELD

The subject matter described herein relates in general to connections made during manufacturing or assembly and, more particularly, to the confirmation of such connections.

BACKGROUND

A variety of connections can be made during the assembly of electrical, mechanical, and fluid systems or assemblies. For instance, the assembly of an automobile, or automobile subassemblies, can require several connections to be made. The connections can be completed by connecting two or more connectors together such that two or more elements are in electrical, fluid, or mechanical communication. As an example, electrical connections can comprise two electrical connectors having electrical contacts. The connectors can be connected such that the electrical contacts are placed in electrical communication with each other.

Many modern assembly or manufacturing facilities include error proofing (in Japanese, "pokayoke") systems to maintain quality control and/or traceability of assemblies. Pokayoke systems typically include controllers stationed at each station of an assembly line. Such controllers are used to detect whether a process was performed according to predefined standards or thresholds. There have been numerous methods used to confirm proper connection of components. As examples, operators can listen for audible signatures of the connection, inspect physical changes in the connectors, and/or manually verify electrical communication between electrical contacts, with the results of such operations being input into a pokayoke system.

SUMMARY

In one respect, the subject matter described herein is directed to a method for confirming connection between two or more components. The method can include receiving acoustic data from the connection between two or more components at a microphone, the microphone being worn by a user. The method can also include determining whether a predetermined acoustic signature is included in the received acoustic data. The method can further include generating a connection status signal based on whether the predetermined acoustic signature is included in the received acoustic data.

In another respect, the subject matter described herein is directed to a system configured to confirm connection of a first connector and a second connector. The system includes a detection unit configured to be wearable by a user. The detection unit can include a processor. The processor can be programmed to initiate executable operations. The executable operations can include receiving acoustic data, and determining whether a predetermined acoustic signature is present in the received acoustic data. The executable operations can also include generating a connection status signal based on whether the predetermined acoustic signature is included in the received acoustic data.

In yet another respect, the subject matter described herein is directed to a method for confirming connection between two or more components. The method can include receiving acoustic data from the connection between two or more components at a microphone, the microphone being worn by a user. The method can further include receiving motion data from the connection between two or more components at a motion sensor, the motion sensor being worn by the user. The method can also include determining whether a predetermined acoustic signature is included in the received acoustic data. Also included in the method is determining whether the motion data is acceptable. The method can include generating a connection status signal based on the determination of whether the predetermined acoustic signature is included in the received acoustic data and the determination of whether the motion data is acceptable.

DETAILED DESCRIPTION

Figure 1:
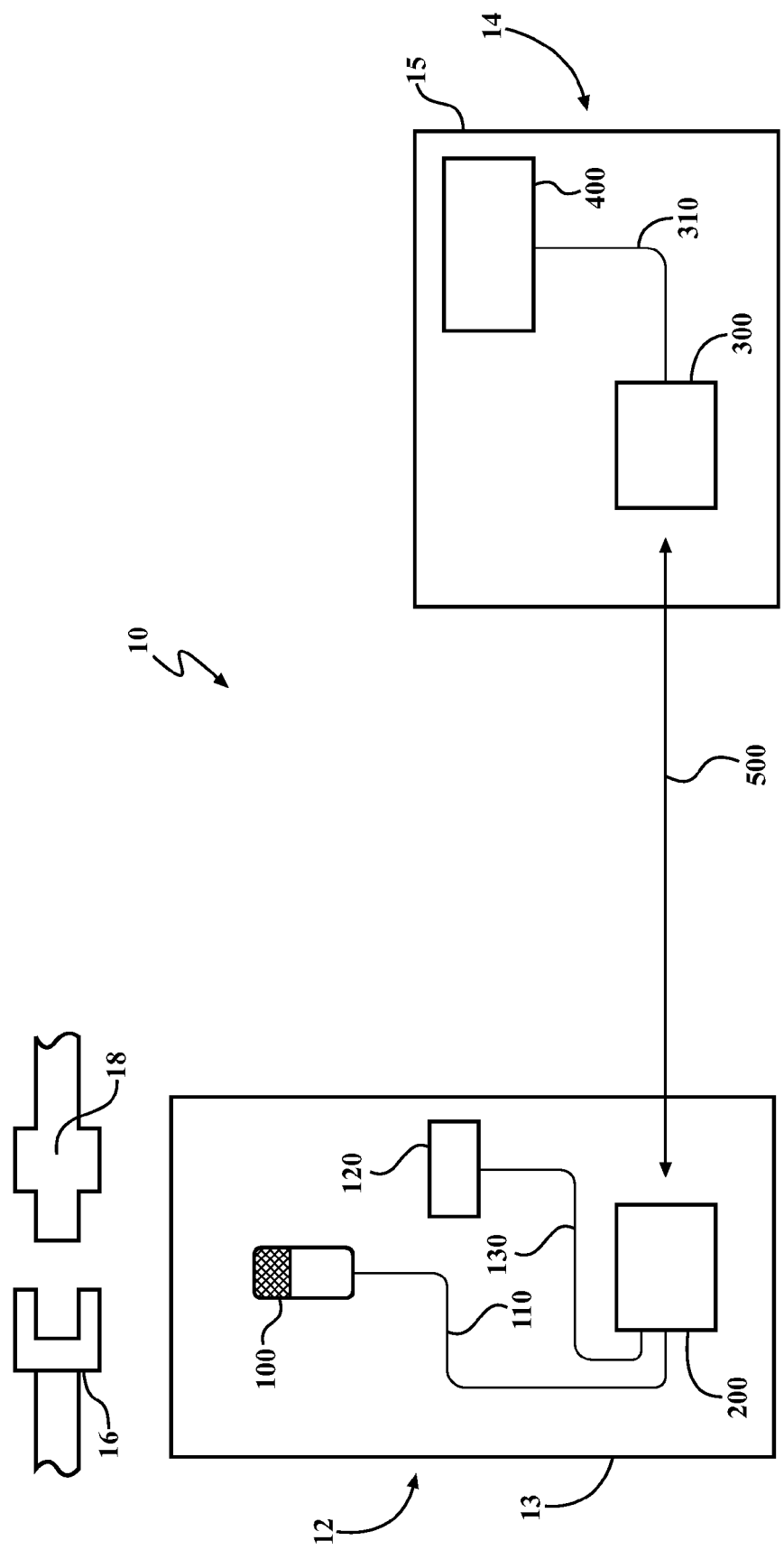
FIG. 1 is an example of a system for confirming the connection of two or more connectors.

This detailed description relates to the confirmation of connections made during a manufacturing or assembly process. More particularly, acoustic data resulting from the connection can be analyzed and used to determine if a proper connection was made. Acoustic data can be produced during the connection of two or more components. The acoustic data can be filtered to reduce noise. The filtered acoustic data can be analyzed to detect whether a predetermined acoustic signature is present. If the predetermined acoustic signature is detected, a confirmation signal can be generated indicating proper connection. In some arrangements, systems and methods can also receive motion data from one or more sensors. The motion data can be analyzed and used to increase the accuracy of proper connection determinations. The confirmation signal can be transmitted to a receiver for use in a pokayoke system. The present detailed description relates to systems, methods, and computer program products that incorporate one or more of such features. In at least some instances, such systems, methods, and computer program products can facilitate determining whether proper connections have been made.

Detailed embodiments are disclosed herein; however, it is to be understood that the disclosed embodiments are intended only as exemplary. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in the Figures, but the embodiments are not limited to the illustrated structure or application.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details.

FIG. 1 is an example of a system 10 for confirming the connection of two or more components. Some of the possible elements of the system 10 are shown in FIG. 1 and will now be described. It will be understood that it is not necessary for the system 10 to have all of the elements shown in FIG. 1 or described herein. The system 10 can include an acoustic detection unit 12 configured for communication over a communication link 500. The system 10 can include a receiving unit 14 configured for communication over the communication link 500.

In some arrangements, the system 10 can be used to confirm proper connection of a first connector 16 and a second connector 18. In one or more arrangements, first and second connectors 16 and 18 can be connectors within a vehicle or vehicle subassembly. As used herein, "vehicle" means any form of motorized transport. In one or more implementations, the vehicle can be an automobile. While arrangements will be described herein with respect to automobile assemblies, it will be understood that embodiments are not limited to automobile assemblies. In some implementations, the vehicle can be a watercraft, an aircraft, a spacecraft, or any other form of transport.

The first and second connectors 16 and 18 can be any physical structure configured to connect portions of a mechanical, fluid, or electrical system, either directly or indirectly. As used herein, the term "connection" is used broadly to include any two or more physical components brought together such that they are in mechanical, fluid, and/or electrical communication. "Proper connection" includes a connection of components in the manner in which the first and second connectors 16 and 18 were designed to connect. For example, a proper connection can allow two or more components to be in mechanical, fluid and/or electrical communication as intended.

In one or more arrangements, the first and second connectors 16 and 18 can be electrical connectors. "Electrical connector" can include any physical structure that joins electrical circuits. For instance, the first and second connectors 16 and 18 can each include one or more electrical conductors (also called "pins"). The first and second connectors 16 and 18 can be configured such that electrical communication is established between them upon proper connection of the first and second connectors 16 and 18. For example, one or more electrical conductors in the first connector 16 can directly or indirectly contact one or more electrical conductors in the second connector 18 when there is proper connection between the first connector 16 and the second connector 18.

In one or more arrangements, the first connector 16 can be a female connector (or "jack"), and the second connector 18 can be a male connector (or "plug"). In one or more arrangements, the first connector 16 and/or the second connector 18 can be an end of automotive wiring harnesses. In one or more arrangements, one of the first connector 16 and the second connector 18 can be a portion of a computing unit, such as an electronic control unit ("ECU"). For instance, the first connector 16 can be a first end of a wire harness, and the second connector 18 can be a receptacle or jack in an ECU.

A connection made between the first and second connectors 16 and 18 can result in acoustic data being generated. As used herein, the term "acoustic data" can be used broadly to describe any form of mechanical waves in gases, liquids, or solids, including sound and/or vibrational signals. In one or more arrangements, the first connector 16 and/or the second connector 18 can be configured such that the proper connection of the first connector 16 and the second connector 18 produces a predetermined acoustic signature. As used herein, "acoustic signature" can include any predetermined acoustic data that is indicative of a proper connection between two or more components. In some arrangements, the acoustic signature produced by the proper connection of the first and second connectors 16 and 18 includes a sound wave. For instance, the sound wave can be an audible noise (e.g., a "click" or a "snap" sound).

In one or more arrangements, the acoustic signature can be produced by a contact between at least a portion of the first connector 16 and at least a portion of the second connector 18. For instance, the acoustic signature can result from the contact of a connection indicator located on the first connector 16 with a portion of the second connector 18. "Connection indicator" can include any structure configured to generate a predetermined vibration and/or sound. In one or more arrangements, the connection indicator can include any combination of a pin, tab, spring or other directionally-biased structure, slot, aperture, latch, strap, and/or cover. For example, the first connector 16 can include a biased tab that, upon reaching a connected position, is configured to contact a portion of the second connector 18 and produce a predetermined click sound. Connectors having substantially the same physical characteristics can produce substantially the same acoustic signature. Connectors having different sizes, shapes, materials, and/or configurations can produce different acoustic signatures.

In one or more arrangements, the acoustic detection unit 12 can be configured to receive acoustic data created by the connection of the first and second connectors 16 and 18. The acoustic detection unit 12 can be configured to analyze the received acoustic data and determine whether or not a proper connection was completed. The acoustic detection unit 12 can be configured to generate and/or transmit a connection status signal to one or more other components or elements within system 10 indicating whether or not a proper connection was completed. The connection status signal can include a confirmation signal indicating a proper connection was made. The connection status signal can also include a rejection signal indicating a proper connection was not detected. In one or more arrangements, the acoustic detection unit 12 can include a detection device to receive and/or identify acoustic data. For instance, the detection unit 12 can include a microphone 100 to monitor for and/or receive acoustic data from a connection made within a detection range of the microphone 100. As used throughout this description, "microphone" includes any component or group of components capable of converting sound or vibration into an electrical signal. The microphone 100 can be of any suitable configuration, such as a dynamic, condenser, and/or piezoelectric microphone. In one or more arrangements, the microphone 100 can be a directional microphone configured to monitor for and/or receive acoustic data from a particular direction in an environment.

In some arrangements, the acoustic detection unit 12 can include a controller 200 communicatively linked to the microphone 100 via a communication link 110. As used herein, the term "communicatively linked" can include direct or indirect connections through a communication channel or pathway or another component or system. Although schematically shown as a single unit in FIG. 1, any one or more elements of the detection unit 12 can be integrated into any number of separate physical units. In one or more arrangements, the microphone 100 can be operatively connected to the controller 200. The term "operatively connected," as used throughout this description, can include direct or indirect connections, including connections without direct physical contact. For instance, the microphone 100 can be operatively connected to the controller 200 via a wired communication link 110. In one or more arrangements the microphone 100 can communicate to the controller 200 via a wireless communication link 110. In some arrangements, the microphone 100 and controller 200 can be packaged within one physical structure (e.g., a housing for the acoustic detection unit 12). The communication link 110 can allow for wired and/or wireless electronic communication between the microphone 100 and the controller 200. Although shown as a single unit, communication link 110 can include any number of interconnected elements that can allow the microphone 100 and the controller to be communicatively linked. Although shown as separate elements within the detection unit 12, the microphone 100, the controller 200, the communication link 110, along with any additional components, can be integrated in one or more electronic units, circuits, or chips. In one or more arrangements, the detection unit 12 can include a housing 13 that can include any physical structure containing the microphone 100 and/or the controller 200.

In some arrangements, the controller 200 can be configured to analyze acoustic data received by the microphone 100. For instance, the controller 200 can determine whether or not a connection was made based on acoustic data received by the microphone 100. In some arrangements, the controller 200 can include and/or can have access to one or more acoustic data profiles that are indicative of a proper connection for two connectors. For example, the controller 200 can include a predetermined acoustic signature corresponding to a proper connection of the first and second connectors 16 and 18. The predetermined acoustic signature stored in memory or in any suitable location. The predetermined acoustic signature can be determined or estimated in any suitable manner. For instance, in one or more arrangements, the predetermined acoustic signature can be determined or estimated from physical or virtual testing and/or analysis. The controller 200 can analyze the acoustic data received by the microphone 100 in any suitable manner. In one or more arrangements, the controller 200 can analyze the acoustic data received by the microphone 100 by applying one or more of a variety of signal analysis methods. For instance, the controller 200 can utilize band pass or hi-pass filtering, frequency analysis, amplitude detection, signature analysis, and/or pattern recognition, just to name a few possibilities. In some arrangements, the controller 200 can determine whether the acoustic data received by the microphone 100 include the predetermined acoustic signature. "Include the predetermined acoustic signature" means that the acoustic data or a portion thereof is substantially identical to a predetermined acoustic signature. For instance, the acoustic data or a portion thereof can be substantially identical to a predetermined acoustic signature within a predetermined probability (e.g., at least about 85%, at least about 90%, at least about 95%, or greater) or confidence level. In some arrangements, the predetermined acoustic signature can include acoustic data within a predetermined variance from a reference acoustic signature. In one or more arrangements, the predetermined acoustic signature can include amplitude and temporal data relating to one or more peaks of a sound wave. For example, the predetermined acoustic signature can include a number of sound wave peaks, time between peaks, and the amplitude of the peaks.

If the predetermined acoustic signature is detected as being included in the acoustic data received by the microphone 100, the controller 200 can determine that a proper connection was completed. If the predetermined acoustic signature is not detected as being included in the acoustic data received by the microphone 100, the controller 200 can continue to monitor acoustic data received by the microphone 100 and/or determine that proper connection was not made. In one or more arrangements, the controller 200 can transmit messages via communication link 500 relating to any determinations described above.

In one or more arrangements, the acoustic detection unit 12 can be a portable unit capable of movement relative to one or more workpieces within a manufacturing or assembly area or station. For example, the acoustic detection unit 12 can be moveable relative to a vehicle or vehicle subassembly in which one or more connections are being made during a manufacturing or assembly process. In one or more arrangements, the acoustic detection unit 12 can be positioned within a detection range from the location where the connection of the first and second connectors 16 and 18 occurs.

In some arrangements, the acoustic detection unit 12 can be configured to be wearable by a user. For instance, the acoustic detection unit 12 can be at least partially included in a package designed to be worn by a user or attachable to clothing or equipment worn by a user. For example, the housing 13 can be configured to be attachable to a user's body and/or clothing. The housing 13 can include clips, straps, adhesives, pins, VELCRO, or any other mechanical or chemical fasteners to allow the housing 13 to be wearable by a user. In one or more arrangements, one or more elements of the detection unit 12 can be included in wearable accessories. For example, the microphone 100 and/or controller 200 can be included in a watch, necklace, belt, backpack, portable communication devices such as mobile phones or media players, and/or glasses. As used herein, the term "watch" includes both standard watches and "smart" watches having advanced operating systems or user interfaces. In some arrangements, the acoustic detection unit 12 can be at least partially implemented as a smart watch, smart eye glasses, smart jewelry (e.g., neckless, earrings, bracelets, etc.), and/or smart clothing (e.g. a shirt, hat, or other article of clothing).

In one or more arrangements, the microphone 100 and the controller 200 can be worn by a user at different positions. For example, the microphone 100 can be incorporated within a strap or watch worn on a user's arm. The controller 200 can be worn by the user on a belt or backpack, and the microphone 100 and the controller 200 can be communicatively linked via a wired or wireless communication link 110. In some arrangements, the microphone 100 and the controller 200 can be packaged and worn in a single unit. For example, both the microphone 100 and controller 200 can be packaged within the housing 13 and included in a smartwatch, worn on a belt, incorporated into a vest, etc.

In one or more arrangements, the detection unit 12 can be configured to receive motion data of one or more components of the detection unit 12. For example, the motion data can result from movement during the connection of the first and second connectors 16 and 18. The detection unit 12 can include a motion sensor 120 communicatively linked with the controller 200 via communication link 130. The above description of the communication link 110 applies equally to the communication link 130. The motion sensor can include any component or group of components capable of detecting movement of the detection unit 12, the microphone 100, and/or the controller 200. For example, the motion sensor 120 can include an accelerometer configured to receive acceleration of one or more components of the detection unit 12 worn by a user.

In some arrangements, the controller 200 can be configured to analyze motion data received by the motion sensor 120. For instance, the controller 200 can determine whether or not motion data is acceptable for the connection between the first and second connectors 16 and 18. In some arrangements, the controller 200 can include and/or can have access to one or more motion data profiles that are indicative of proper motion during the connection for two connectors. For example, the controller 200 can include a range, or a maximum limit, of acceleration values during connection of the first and second connectors 16 and 18. The predetermined range or maximum acceleration limit can be stored in memory or in any suitable location.

The controller 200 can analyze the motion data received by the motion sensor 120 in any suitable manner. In one or more arrangements, the controller 200 can analyze acceleration data received by the motion sensor 120 by applying one or more of a variety of signal analysis methods. For instance, the controller 200 can utilize band pass or hi-pass filtering, frequency analysis, amplitude detection, signature analysis, and/or pattern recognition, just to name a few possibilities.

In one or more arrangements, the controller 200 can use motion data received from the motion sensor 120 to reduce false positive connection confirmations. For example, the predetermined acoustic signature can be detected by the controller 200 resulting from a different operation than the connection of the first and second connectors 16 and 18. If the motion data is not acceptable, the controller 200 can determine a proper connection has not been made. As a non-limiting example, an operator can be doing another operation such as hammering a trim strip in place. The motion data, such as acceleration, received from the motion sensor 120 during this operation can be outside the acceptable values for a proper connection.

In one or more arrangements, the controller 200 can use motion data received from the motion sensor 120 to reinforce true positive connection confirmations. For example, if the predetermined acoustic signature is detected, the controller 200 can determine if the motion data falls within acceptable values for the connection.

Figure 2:
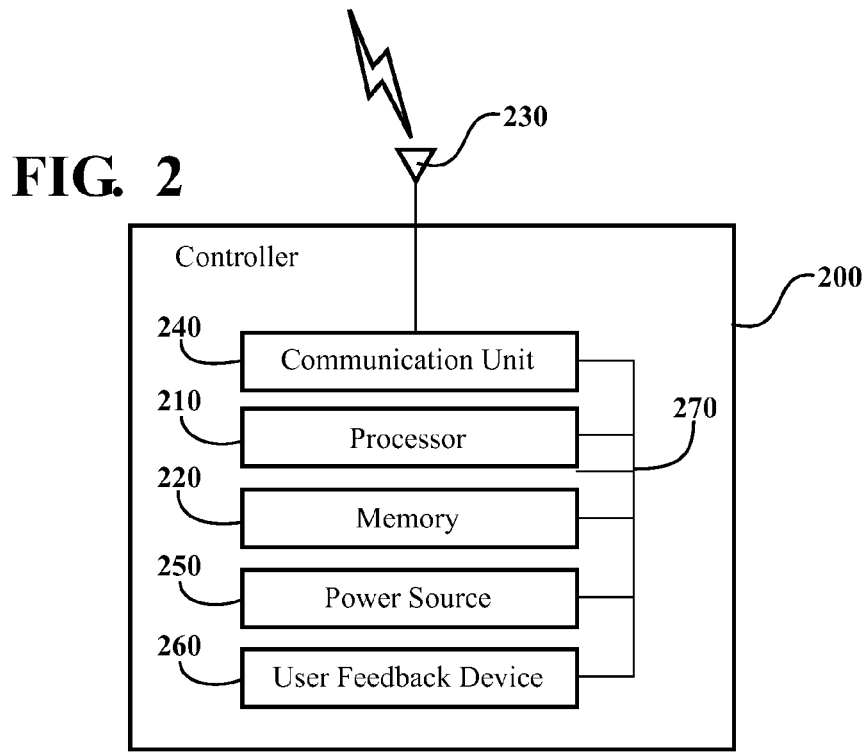
FIG. 2 is an example of a controller used within the system of FIG. 1.

In one or more arrangements, the detection unit 12 and/or receiving unit 14 can include one or more user feedback devices configured to provide feedback to users or operators. The user feedback device can provide indication of whether or not a proper connection was made. For example, the controller 200 of the detection unit 12 can include the user feedback device 260 (FIG. 2). The indication of whether or not a proper connection was confirmed can be provide in any suitable manner. For instance, the indication can be a visual, haptic, and/or visual indication. The user feedback device 260 can include, as examples, lights, vibration elements, and/or sound generators (e.g., speakers or sound cards) to produce an indication.

In one or more arrangements of system 10, the receiving unit 14 can be configured to receive communications from the detection unit 12 regarding the status of one or more connections for a particular manufacturing or assembly process. For example, the receiving unit 14 can receive confirmation signals from the detection unit 12, such as over the communication link 500. The confirmation signals can indicate proper connection of components.

The receiving unit 14 can include various components. For instance, the receiving unit 14 can include a receiver 300, a pokayoke controller 400, and/or communication link 310. Each of these components will be described in turn below. Although the receiving unit 14 is shown with the above elements, the receiving unit 14 is not limited to including all of the elements shown, and can include elements not listed. In one or more arrangements, the receiving unit 14 can include a housing 15 that can include any physical structure containing the receiver 300 and/or pokayoke controller 400.

In one or more arrangements, the receiver 300 can be any device configured to receive connection status signals from the detection unit 12. For instance, the receiver 300 can receive confirmation signals from the controller 200 via the communication link 500.

As noted above, the receiving unit 14 can include the pokayoke controller 400 to identify and trace abnormalities of assembly or manufacturing. For instance, the pokayoke controller 400 can be implemented as a line-side controller at one or more stations of an assembly line. The pokayoke controller 400 can monitor a variety of conditions of an assembly. For example, the pokayoke controller 400 can be used to monitor and track several manufacturing or assembly steps, such as torque levels of fasteners, the presence or absence of components, the presence or absence of manufacturing or assembly processes, or other abnormalities that occur during an assembly or manufacturing process.

The pokayoke controller 400 can be configured for use within one assembly station within a facility. For example, the pokayoke controller 400 can monitor one process within one station of an assembly line. In some arrangements, the pokayoke controller 400 can be deployed to monitor several operations or stations of an assembly line. The pokayoke controller 400 can be physically present proximate a manufacturing or assembly process. In some arrangements, the pokayoke controller 400 can be located elsewhere, such as in a computing cloud, and in communication with other components within system 10 via one or more networks.

FIG. 2 is a diagram of an example of at least a portion of the controller 200 in which the aspects, features, and elements disclosed herein can be implemented. In one or more arrangements, controller 200 can include a processor 210, a memory 220, an electronic communication interface 230, an electronic communication unit 240, a power source 250, a user feedback device 260, a communication bus 270, or any combination thereof. Although shown as a single unit, any one or more elements of the controller 200 can be integrated into any number of separate physical units. Although the controller 200 is shown with the above elements, the controller 200 is not limited to including all of the elements shown, and can include elements not listed.

In some arrangements, the controller 200 can include units or elements not shown in FIG. 2, such as an enclosure, input device(s), a frequency modulated (FM) radio unit, a Near Field Communication (NFC) Module, or any combination thereof.

The processor 210 can include any device or combination of devices capable of manipulating or processing a signal or other information now-existing or hereafter developed, including optical processors, quantum processors, molecular processors, or a combination thereof. For example, the processor 210 can include one or more general purpose processors, one or more special purpose processors, one or more digital signal processor (DSP), one or more microprocessors, one or more controllers, one or more microcontrollers, one or more integrated circuits, one or more an Application Specific Integrated Circuits, one or more Field Programmable Gate Array, one or more programmable logic arrays, one or more programmable logic controllers, firmware, one or more state machines, or any combination thereof.

The processor 210 can be operatively connected to the memory 220, the electronic communication interface 230, the electronic communication unit 240, the power source 250, the user feedback device 260, or any combination thereof. For example, the processor can be operatively connected to the memory 220 via a communication bus 270.

The memory 220 can include any tangible non-transitory computer-usable or computer-readable medium, capable of, for example, containing, storing, communicating, or transporting machine readable instructions or any information associated therewith, for use by or in connection with the processor 210. The memory 220 can be, for example, one or more solid state drives, one or more memory cards, one or more removable media, one or more read only memories, one or more random access memories, one or more disks, including a hard disk, a magnetic or optical card, or any type of non-transitory media suitable for storing electronic information, or any combination thereof.

The communication interface 230 can be a wireless antenna or any other wireless unit capable of interfacing with an electronic communication medium, such as the communication link 500 shown in FIG. 1. While FIG. 1 shows the communication interface 230 communicating via a single communication link 500, it will be understood that the communication interface 230 can be configured to communicate via any number of communication links.

Figure 3:
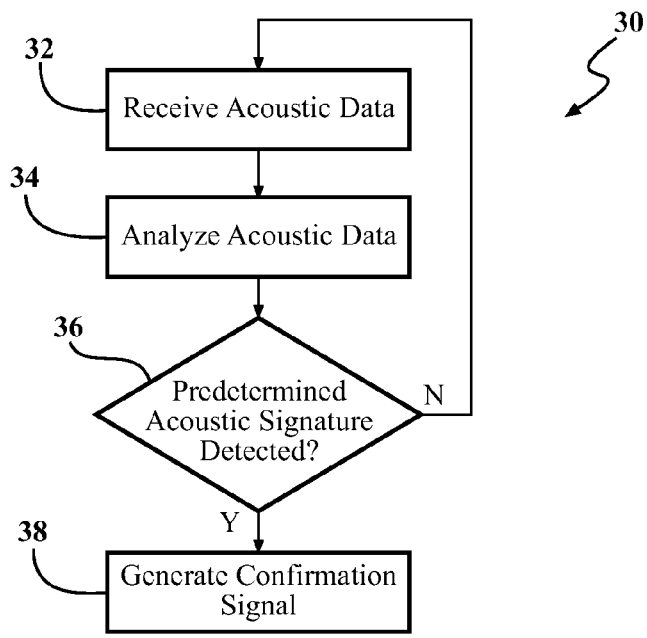
FIG. 3 is an example of a method for confirming connections with acoustic data.

The communication unit 240 can be configured to transmit or receive signals via an electronic communication medium. The communication unit 240 can be configured to transmit, receive, or both via a wireless communication medium. Although FIG. 3 shows a single communication unit 240 and a single communication interface 230, any number of communication units and any number of communication interfaces can be used. In one or more arrangements, the communication interface 230 and the communication unit 240 can be configured to transmit, receive, or both, radio frequency (RF) signals. In some arrangements, the communication interface 230 and the communication unit 240 can be configured to transmit and/or receive BLUETOOTH signals.

The power source 250 can be any suitable device for powering the controller 200. For example, the power source 250 can include a wired power source; one or more dry cell batteries, such as nickel-cadmium (NiCd), nickel-zinc (NiZn), nickel metal hydride (NiMH), lithium-ion (Li-ion); solar cells; or any other device capable of powering the controller 200. The processor 210, the memory 220, the electronic communication interface 230, the electronic communication unit 240, the user feedback device 260, or any combination thereof, can be operatively connected to the power source 250.

The user feedback device 260 can be any suitable device for providing one or more users feedback relating to the status of a connection. For example, the user feedback device 260 can be configured to provide confirmation to a user when a proper connection is determined. In one or more arrangements, the user feedback device 260 can provide visual feedback to a user. For example, the user feedback device 260 can include a display, such as a liquid crystal display (LCD) display unit and/or an organic light-emitting diode (OLED) display unit. In some arrangements, the user feedback device 260 can be configured to provide haptic feedback to a user. For example, the user feedback device 260 can include one or more elements configured to selectively vibrate or move within the detection unit 12. In one or more arrangements, the user feedback device 260 can be configured to provide visual and/or audial feedback to a user. For example, the user feedback device 260 can include one or more elements configured to generate an image, text, light, and/or sound.

Although shown as separate elements, the processor 210, the memory 220, the electronic communication interface 230, the electronic communication unit 240, or any combination thereof can be integrated in one or more electronic units, circuits, or chips.

In one or more arrangements, the pokayoke controller 400 can include similar elements as the controller 200 (shown in FIG. 2). For example, the pokayoke controller 400 can include a processor, a memory, a power supply and/or a communication unit. The above description of these elements with respect to the controller 200 can apply equally to the pokayoke controller 400. In one or more arrangements, the processor of the pokayoke controller 400 can carry out instructions stored in a memory of the pokayoke controller. The instructions can cause the pokayoke controller 400 to record information received from the detection unit 12. In some arrangements, the pokayoke controller 400 can be configured to record (or "flag") abnormalities associated with a particular vehicle or vehicle subassembly. For example, the pokayoke controller 400 can flag particular vehicles when a confirmation signal indicating proper connection of components has not be received by the receiver 300 or if a signal indicates a non-proper connection.

The various components of system 10 can be communicatively linked through the communication link 500. For instance, the controller 200 of the detection unit 12 can be communicatively linked with the receiver 300 of the receiving unit 14 via communication link 500. Communication link 500 can allow for wired and/or wireless communication. For example, the controller 200 can communicate with the receiver 300 via radio frequency signals. In some arrangements, two or more components in the system 10 can be communicatively linked to each other using one or more networks. A "network" can mean one or more components designed to transmit and/or receive information from one source to another. Communication link 500 can be any type of communication configured to provide for any type of electronic communication. For example, the communication link 500 can be incorporated in a local area network (LAN), wide area network (WAN), virtual private network (VPN), a mobile or cellular telephone network, the Internet, or any other electronic communication system. Although shown as a single unit, communication link 500 can include any number of interconnected elements.

Now that various potential systems, devices, elements and/or components have been described, various methods for confirming connections will now be described. Referring to FIG. 3, one example of a method for confirming connections is shown, and various possible steps for method 30 will now be described. The method 30 can be applicable to the arrangements described herein and in the Figures, but it is to be understood that the method 30 can be carried out with other suitable systems. Additionally, the method 30 can include other steps that are not shown here, and the method 30 is not limited to including every step shown in FIG. 3. The steps that are illustrated here as part of the method 30 are not limited to this particular chronological order. Indeed, some of the steps can be performed in a different order than what is shown and/or at least some of the steps shown can occur simultaneously.

At block 32, acoustic data can be received. In some arrangements, the controller 200 can receive the acoustic signals via the microphone 100 or any other suitable device. At block 34, the acoustic signals can be analyzed. In one or more arrangements, the controller 200 can analyze the acoustic signals based on instructions stored in memory. For example, the controller 200 can be programmed to perform one or more signal analysis techniques, such as band pass or hi-pass filtering, frequency analysis, amplitude detection, signature analysis, and/or pattern recognition. In one or more arrangements, the controller 200 can be programmed to filter the received acoustic data in any suitable manner. For instance, the controller 200 can be programmed to reduce noise to facilitate the detection of an acoustic signature.

At block 36, it can be determined whether a predetermined acoustic signature is detected. As described above, the controller 200 can include one or more predetermined acoustic signatures corresponding to the sound or vibration produced by the proper connection of two or more connectors. For example, for a particular first connector 16 and second connector 18, an acoustic signature can be stored on and/or accessible by the controller 200. The controller 200 can then determine whether or not this predetermined acoustic signature is found in the received acoustic data. If the predetermined acoustic signature is not detected, the method 30 can return to block 32 and continue to receive acoustic data. Alternatively, if the predetermined acoustic signature is not detected, a signal indicating a non-proper connection of components can be generated.

Responsive to detecting the predetermined acoustic signature, a confirmation signal can be generated at block 38. The confirmation signal can indicate proper connection of components. In one or more arrangements, the controller 200 can transmit the confirmation signal to one or more components within the system 10, such as the receiving unit 14. In some arrangements, the confirmation signal can be a wireless signal, such as an RF and/or BLUETOOTH signal.

Figure 4A:
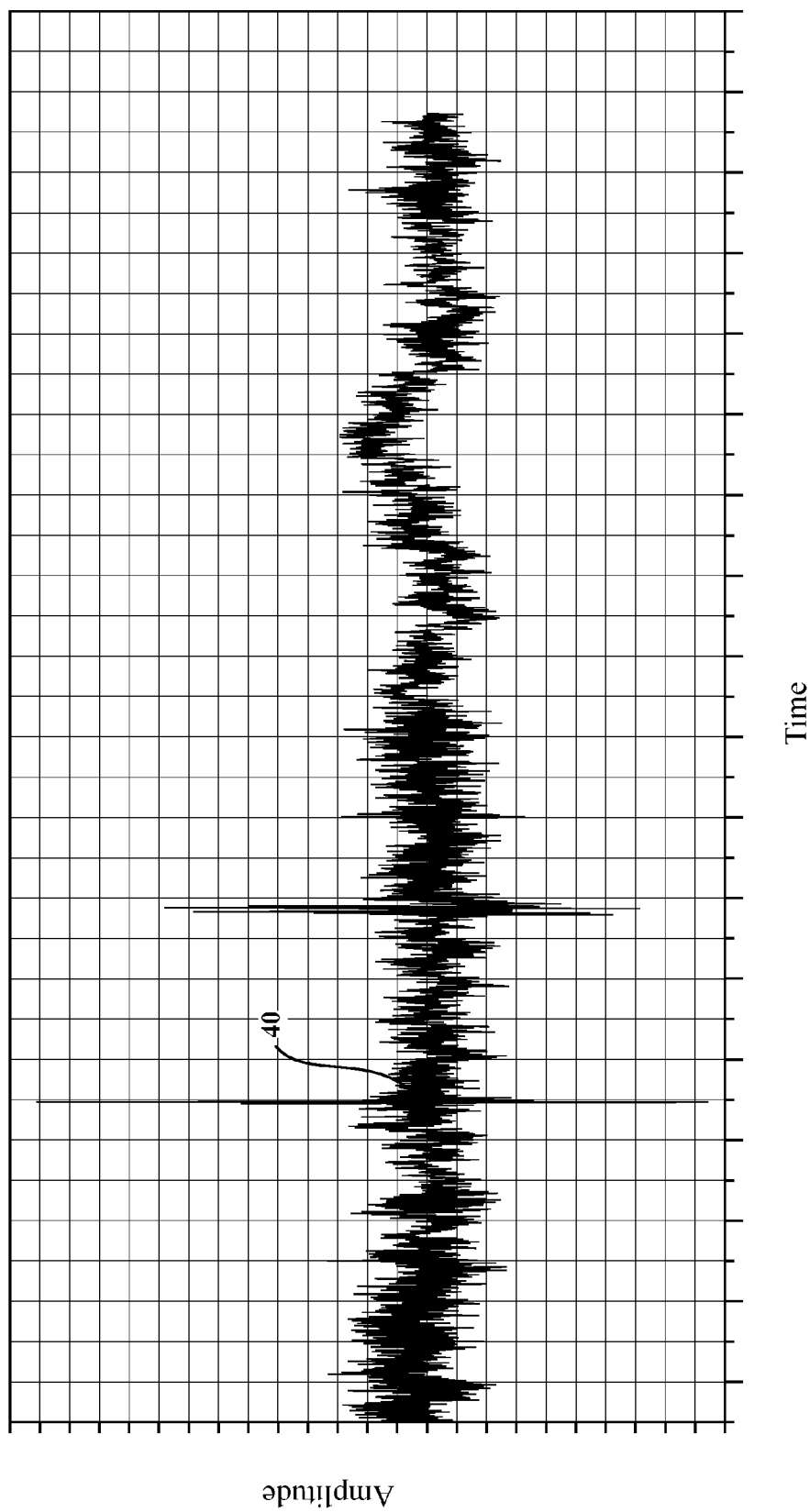
FIG. 4A is an example of acoustic data received from a connection.
Figure 4B:
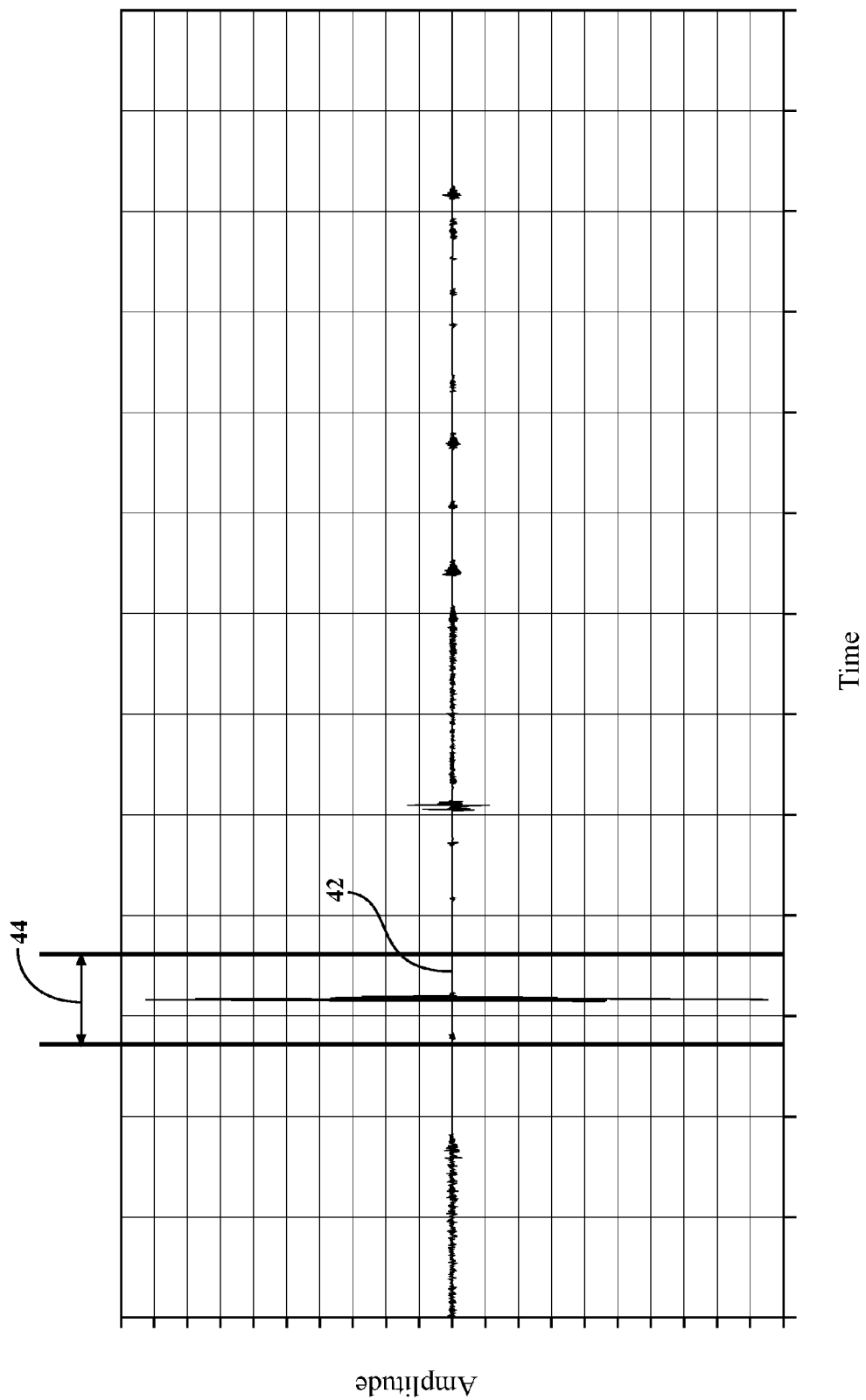
FIG. 4B is an example of a filtered form of the received acoustic data of FIG. 4A.
Figure 4C:
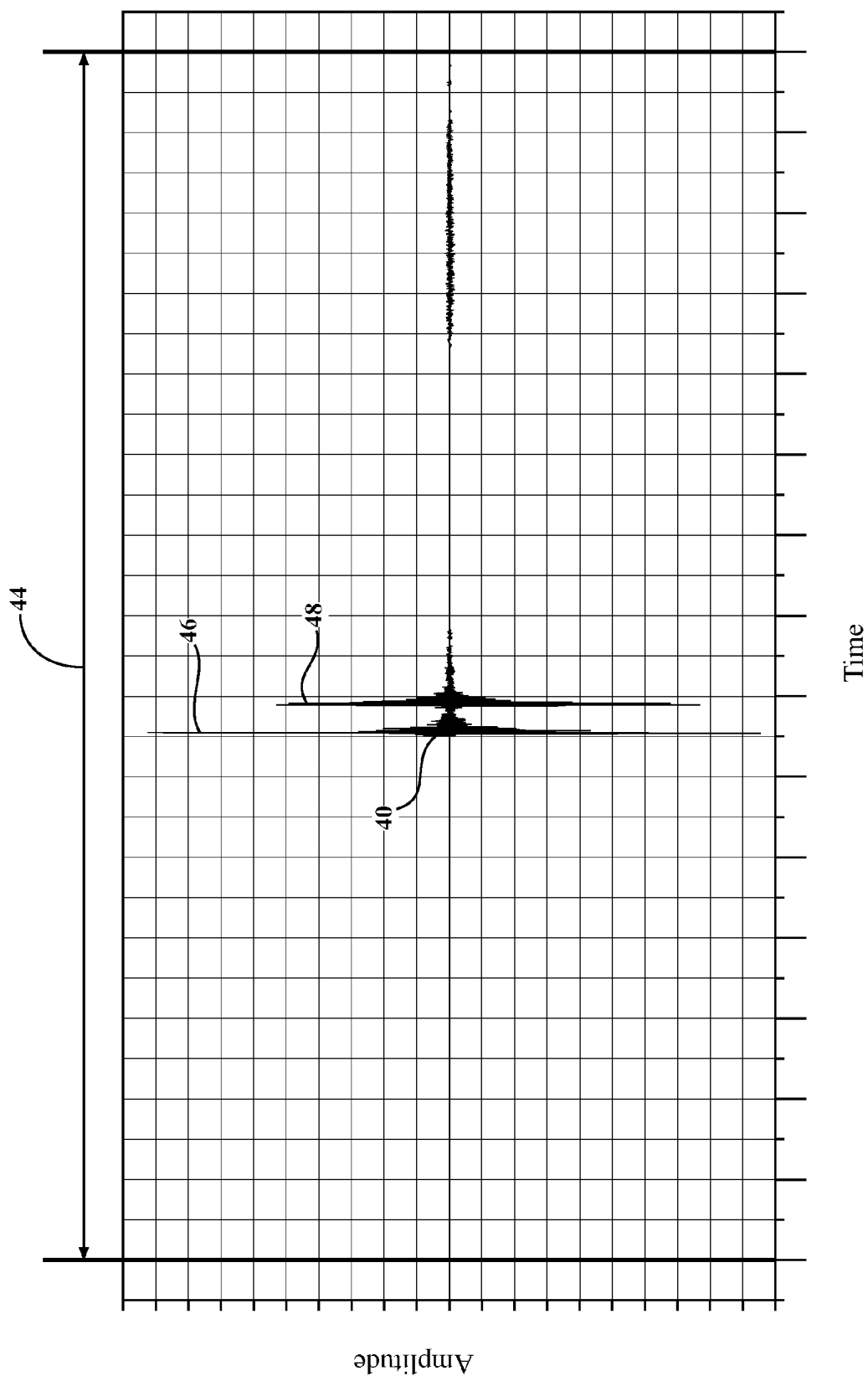
FIG. 4C is a close-up view of a portion of the filtered acoustic data of FIG. 4B.

Referring now to FIGS. 4A-C, examples of acoustic signal analysis by the controller 200 can be further described. As shown in FIG. 4A, the controller 200 can receive acoustic data 40 in the form of a sound wave via the microphone 100. The acoustic data 40 can initially include noise of varying amplitude. As described above, the controller 200 can analyze the acoustic data 40 using any suitable technique(s). In one or more arrangements, the controller 200 can filter noise included in the acoustic data 40. An example of the acoustic data 40 after being filtered is shown in FIG. 4B. In one or more arrangements, the controller 200 can be configured to identify an area of interest 42 of the acoustic data 40. The area of interested can be identified based on one or more factor(s). For instance, the area of interest can be based on the appearance of a portion of the filtered acoustic data and/or a particular time range 44 within which a portion of the acoustic data was received. Zooming in on the area of interest 42 in FIG. 4C shows further detail of an acoustic signature. As shown in FIG. 4C, the acoustic signature can be represented by two peaks 46 and 48 that represent two "clicks" during a connection. The two peaks 46 and 48 in the acoustic data 40 can be compared to one or more predetermined acoustic signatures to determine whether one of the predetermined acoustic signatures is included in the received acoustic data 40. In some arrangements, the acoustic signature can include one peak corresponding to one "click" sound during a connection. Furthermore, the acoustic signature can contain three or more peaks. If it is determined that a predetermined acoustic signature is included in the received acoustic data, then it can be determined that a proper connection was met.

Figure 5:
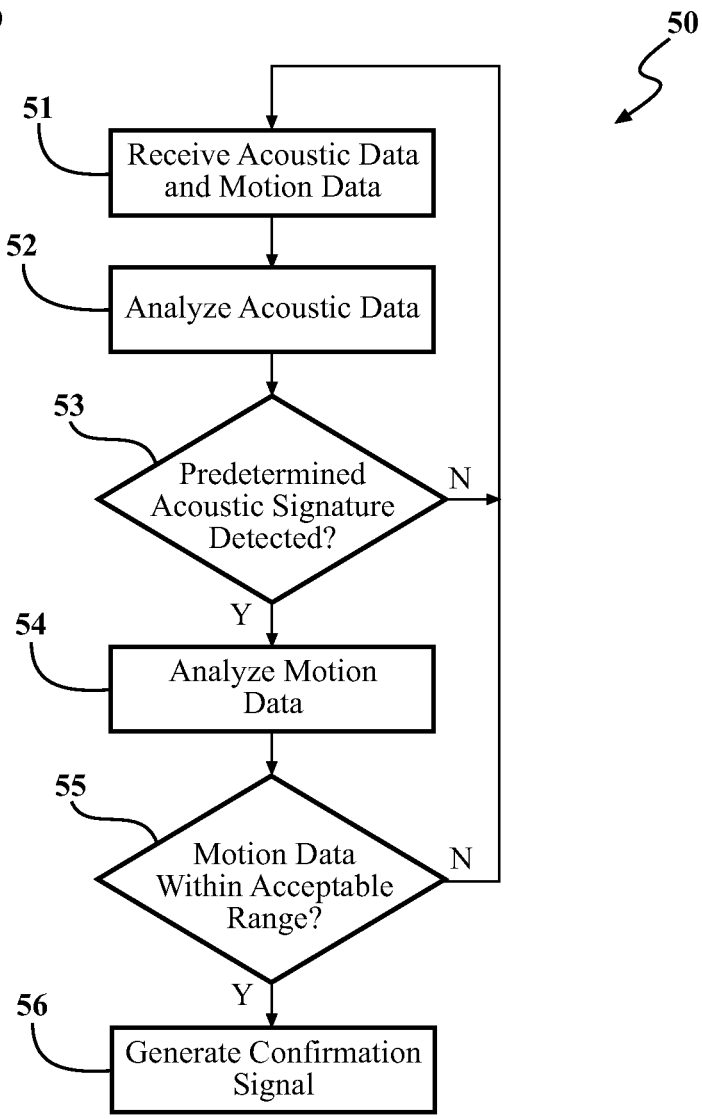
FIG. 5 is an example of a method for confirming connections with acoustic data and motion data.

Referring to FIG. 5, one example of a method for confirming connections using acoustic data and motion data is shown, and various possible steps for method 50 will now be described. The method 50 can be applicable to the arrangements described herein and in the Figures, but it is to be understood that the method 50 can be carried out with other suitable systems. Additionally, the method 50 can include other steps that are not shown here, and the method 50 is not limited to including every step shown in FIG. 5. The steps that are illustrated here as part of the method 50 are not limited to this particular chronological order. Indeed, some of the steps can be performed in a different order than what is shown and/or at least some of the steps shown can occur simultaneously.

At block 51, acoustic data and motion data can be received. In some arrangements, the controller 200 can receive the acoustic signals via the microphone 100 or any other suitable device. In some arrangements, the controller 200 can received the motion data via the motion sensor 120, such as an accelerometer. At block 52, the acoustic signals can be analyzed. In one or more arrangements, the controller 200 can analyze the acoustic signals based on instructions stored in memory. For example, the controller 200 can be programmed to perform one or more signal analysis techniques, such as band pass or hi-pass filtering, frequency analysis, amplitude detection, signature analysis, and/or pattern recognition. In one or more arrangements, the controller 200 can be programmed to filter the received acoustic data in any suitable manner. For instance, the controller 200 can be programmed to reduce noise to facilitate the detection of an acoustic signature.

At block 53, it can be determined whether a predetermined acoustic signature is detected. As described above, the controller 200 can include one or more predetermined acoustic signatures corresponding to the sound or vibration produced by the proper connection of two or more connectors. For example, for a particular first connector 16 and second connector 18, an acoustic signature can be stored on and/or accessible by the controller 200. The controller 200 can then determine whether or not this predetermined acoustic signature is found in the received acoustic data. If the predetermined acoustic signature is not detected, the method 30 can return to block 51 and continue to receive acoustic data. Alternatively, if the predetermined acoustic signature is not detected, a signal indicating a non-proper connection of components can be generated.

Responsive to detecting the predetermined acoustic signature, the motion data can be analyzed at block 54. In one or more arrangements, the controller 200 can analyze the motion data based on instructions stored in memory. For example, the controller 200 can be programmed to perform one or more signal analysis techniques, such as band pass or hi-pass filtering, frequency analysis, amplitude detection, signature analysis, and/or pattern recognition. In one or more arrangements, the controller 200 can be programmed to filter the received motion data in any suitable manner. For instance, the controller 200 can be programmed to reduce noise to facilitate the detection of a maximum acceleration.

At block 55, it can be determined whether the motion data is within an acceptable range. As described above, the controller 200 can include ranges, or a maximum or minimum limit, for acceptable motion. For example, it can be determined by the controller 200 if the acceleration of the detection unit 12 is greater than a predetermined threshold. If the motion data is not acceptable, the method 50 can return to block 51 and continue to receive acoustic data and motion data. Alternatively, if the motion data is not acceptable, a signal indicating a non-proper connection of components can be generated.

Responsive to determining the motion data is acceptable, a confirmation signal can be generated at block 56. The confirmation signal can indicate proper connection of components. In one or more arrangements, the controller 200 can transmit the confirmation signal to one or more components within the system 10, such as the receiving unit 14. In some arrangements, the confirmation signal can be a wireless signal, such as an RF and/or BLUETOOTH signal.

It will be appreciated that arrangements described herein can provide numerous benefits, including one or more of the benefits mentioned herein. For example, arrangements described herein can automatically determine whether proper connections have been made. Systems and methods described herein can use the unique acoustic signature associated with a proper connection of connectors to confirm connections made in an assembly process without the need for operators to complete additional tasks. Furthermore, confirmation signals can be transmitted to pokayoke systems automatically to ensure traceability of abnormal connections. In arrangements where portions of the detection unit are worn on a user, the connection confirmation can occur without the need for separate equipment. The addition of one or more motion sensors with the detection units can increase the accuracy of the connection confirmations. For example, the acceleration can be measured and it can be determined if the acceleration was acceptable for the particular connection of two components.

The flowcharts and block diagrams in the figures illustrate the architecture, functionality, and operation of possible implementations of systems, methods and computer program products according to various embodiments. In this regard, each block in the flowcharts or block diagrams can represent a module, segment, or portion of code, which comprises one or more executable instructions for implementing the specified logical function(s). It should also be noted that, in some alternative implementations, the functions noted in the block can occur out of the order noted in the figures. For example, two blocks shown in succession can, in fact, be executed substantially concurrently, or the blocks can sometimes be executed in the reverse order, depending upon the functionality involved.

The systems, components and/or processes described above can be realized in hardware or a combination of hardware and software and can be realized in a centralized fashion in one processing system or in a distributed fashion where different elements are spread across several interconnected processing systems. Any kind of processing system or other apparatus adapted for carrying out the methods described herein is suited. A typical combination of hardware and software can be a processing system with computer-usable program code that, when being loaded and executed, controls the processing system such that it carries out the methods described herein. The systems, components and/or processes also can be embedded in a computer-readable storage, such as a computer program product or other data programs storage device, readable by a machine, tangibly embodying a program of instructions executable by the machine to perform methods and processes described herein. These elements also can be embedded in an application product which comprises all the features enabling the implementation of the methods described herein and, which when loaded in a processing system, is able to carry out these methods.

Furthermore, arrangements described herein can take the form of a computer program product embodied in one or more computer-readable media having computer-readable program code embodied, e.g., stored, thereon. Any combination of one or more computer-readable media can be utilized. The computer-readable medium can be a computer-readable signal medium or a computer-readable storage medium. The phrase "computer-readable storage medium" means a non-transitory storage medium. A computer-readable storage medium can be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk drive (HDD), a solid state drive (SSD), a random access memory (RAM), a read-only memory (ROM), an erasable programmable read-only memory (EPROM or Flash memory), an optical fiber, a portable compact disc read-only memory (CD-ROM), a digital versatile disc (DVD), an optical storage device, a magnetic storage device, or any suitable combination of the foregoing. In the context of this document, a computer-readable storage medium can be any tangible medium that can contain, or store a program for use by or in connection with an instruction execution system, apparatus, or device.

Program code embodied on a computer-readable medium can be transmitted using any appropriate medium, including but not limited to wireless, wireline, optical fiber, cable, RF, etc., or any suitable combination of the foregoing. Computer program code for carrying out operations for aspects of the present arrangements can be written in any combination of one or more programming languages, including an object oriented programming language such as Java™, Smalltalk, C++ or the like and conventional procedural programming languages, such as the "C" programming language or similar programming languages. The program code can execute entirely on the user's computer, partly on the user's computer, as a stand-alone software package, partly on the user's computer and partly on a remote computer, or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider).

As used herein, the terminology "example", "embodiment", "implementation", "aspect", "feature", or "element" indicate serving as an example, instance, or illustration. Unless expressly indicated, any example, embodiment, implementation, aspect, feature, or element is independent of each other example, embodiment, implementation, aspect, feature, or element and can be used in combination with any other example, embodiment, implementation, aspect, feature, or element.

As used herein, the terminology "or" is intended to mean an inclusive "or" rather than an exclusive "or". That is, unless specified otherwise, or clear from context, "X includes A or B" is intended to indicate any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form.

Further, for simplicity of explanation, although the figures and descriptions herein can include sequences or series of steps or stages, elements of the methods disclosed herein can occur in various orders or concurrently. Additionally, elements of the methods disclosed herein can occur with other elements not explicitly presented and described herein. Furthermore, not all elements of the methods described herein can be required to implement a method in accordance with this disclosure. Although aspects, features, and elements are described herein in particular combinations, each aspect, feature, or element can be used independently or in various combinations with or without other aspects, features, and elements.

Although features can be described above or claimed as acting in certain combinations, one or more features of a combination can in some cases be excised from the combination, and the combination can be directed to a sub-combination or variation of a sub-combination.

The above-described aspects, examples, and implementations have been described in order to allow easy understanding of the application are not limiting. On the contrary, the application covers various modifications and equivalent arrangements included within the scope of the appended claims, which scope is to be accorded the broadest interpretation so as to encompass all such modifications and equivalent structure as is permitted under the law.

What is claimed is:

1. A method for confirming connection between two or more components, comprising:
   receiving acoustic data from the connection between two or more components at a microphone, the microphone being worn by a user;
   determining whether a predetermined acoustic signature is included in the received acoustic data; and
   generating a connection status signal based on the determination of whether the predetermined acoustic signature is included in the received acoustic data, wherein the generating a connection status signal includes generating a rejection signal if it is determined that the predetermined acoustic signature is not included in the received acoustic data.

2. The method of claim 1, wherein the generating a connection status signal includes generating a confirmation signal if it is determined that the predetermined acoustic signature is included in the received acoustic data.

3. The method of claim 2, wherein generating a confirmation signal indicating proper connection includes presenting an indicator to the user.

4. The method of claim 3, wherein the indicator is a haptic indicator, and wherein presenting an indicator to the user includes causing a component worn by a user to vibrate.

5. The method of claim 3, wherein the indicator is a visual indicator, and wherein presenting an indicator to the user includes causing a component worn by a user to present one of a visual image, text, or light.

6. A method for confirming connection between two or more components, comprising
   receiving acoustic data from the connection between two or more components at a microphone, the microphone being worn by a user;
   determining whether a predetermined acoustic signature is included in the received acoustic data; and
   generating a connection status signal based on the determination of whether the predetermined acoustic signature is included in the received acoustic data, wherein determining whether a predetermined acoustic signature is included in the received acoustic data further includes filtering the acoustic data according to predetermined criteria.

7. The method of claim 6, wherein the filtering the acoustic data according to predetermined criteria includes at least one of:
   band pass filtering, hi-pass filtering, frequency analysis, amplitude detection, signature analysis, and pattern recognition.

8. A system configured to confirm connection of a first connector and a second connector, the system comprising:
   a detection unit configured to be wearable by a user, the detection unit including:
      a processor, the processor being programmed to initiate executable operations comprising:
         receiving acoustic data;
         determining whether a predetermined acoustic signature is present in the received acoustic data; and
         generating a connection status signal based on the determination of whether the predetermined acoustic signature is included in the received acoustic data, wherein the determining whether a predetermined acoustic signature is included in the received acoustic data further includes filtering the acoustic data according to a predetermined criteria.

9. The system of claim 8, wherein filtering the acoustic data according to a predetermined criteria includes at least one of:
   band pass filtering, hi-pass filtering, frequency analysis, amplitude detection, signature analysis, and pattern recognition.

10. The system of claim 8, wherein the detection unit further includes a user feedback device, and the processor is further programmed to initiate the executable operations including presenting a positive indicator to the user via the user feedback device if it is determined that the predetermined acoustic signature is included in the acoustic data.

11. The system of claim 8, wherein the detection unit is included in a watch, eye glasses, jewelry, a personal communication device, or clothing.

12. The system of claim 8, wherein generating a connection status signal includes generating a confirmation signal if it is determined that the predetermined acoustic signature is included in the acoustic data.

13. The system of claim 8, wherein the detection unit further comprises a microphone communicatively linked to the processor to provide the acoustic data to the processor.

14. The system of claim 13, wherein the microphone and the processor are packaged together in a housing wearable by a user.

15. A system configured to confirm connection of a first connector and a second connector, the system comprising:
   a detection unit configured to be wearable by a user, the detection unit including:
      a processor, the processor being programmed to initiate executable operations comprising:
         receiving acoustic data;
         determining whether a predetermined acoustic signature is present in the received acoustic data; and
         generating a connection status signal based on the determination of whether the predetermined acoustic signature is included in the received acoustic data, wherein the processor is further programmed to initiate the executable operations including:
receiving motion data; and
determining if the motion data is acceptable,
wherein the generating a connection status signal is further based on the determination of whether the motion data is acceptable.

16. The system of claim 15, further including a motion sensor communicatively linked to the processor to provide the motion data to the processor.

17. A system configured to confirm connection of a first connector and a second connector, the system comprising:
a detection unit configured to be wearable by a user, the detection unit including:
a processor, the processor being programmed to initiate executable operations comprising:
receiving acoustic data;
determining whether a predetermined acoustic signature is present in the received acoustic data; and
generating a connection status signal based on the determination of whether the predetermined acoustic signature is included in the received acoustic data
a receiving unit communicatively linked to the detection unit, the receiving unit including:
a pokayoke controller, the pokayoke controller configured to receive the connection status signal generated by the detection unit, and
wherein generating the connection status signal includes transmitting the connection status signal to the pokayoke controller.

18. A method for confirming connection between two or more components, comprising:
receiving acoustic data from the connection between two or more components at a microphone, the microphone being worn by a user;
receiving motion data from the connection between two or more components at a motion sensor, the motion sensor being worn by the user;
determining whether a predetermined acoustic signature is included in the received acoustic data;
determining whether the motion data is acceptable; and
generating a connection status signal based on the determination of whether the predetermined acoustic signature is included in the received acoustic data and the determination of whether the motion data is acceptable.

* * * * *